United States Patent [19]
Wilson et al.

[11] Patent Number: 6,034,021
[45] Date of Patent: Mar. 7, 2000

[54] METAL COMPLEXES CONTAINING BRIDGED, NON-AROMATIC, ANIONIC, DIENYL GROUPS AND ADDITION POLYMERIZATION CATALYSTS THEREFROM

[75] Inventors: David R. Wilson; Peter N. Nickias; David R. Neithamer, all of Midland, Mich.; Richard D. Ernst, Salt Lake City, Utah

[73] Assignees: The Dow Chemical Company, Midland, Mich.; The University of Utah, Salt Lake City, Utah

[21] Appl. No.: 09/113,265

[22] Filed: Jul. 10, 1998

Related U.S. Application Data

[62] Division of application No. 08/896,898, Jul. 18, 1997, Pat. No. 5,817,849.
[60] Provisional application No. 60/022,032, Jul. 22, 1996.
[51] Int. Cl.[7] .............................. C07F 17/00; C07F 7/00; B01J 31/00; C08F 4/64
[52] U.S. Cl. .................. 502/103; 502/117; 502/158; 526/127; 526/160; 526/943; 556/12; 556/13; 556/53

[58] Field of Search ................... 556/12, 13, 53; 502/103, 117, 158; 526/127, 160, 943

[56] References Cited

U.S. PATENT DOCUMENTS

| | | | |
|---|---|---|---|
| 5,055,438 | 10/1991 | Canich ................................ | 502/117 |
| 5,057,475 | 10/1991 | Canich et al. ..................... | 502/104 |
| 5,098,867 | 3/1992 | Canich ................................ | 502/103 |
| 5,132,380 | 7/1992 | Stevens et al. .................... | 526/126 |
| 5,495,036 | 2/1996 | Wilson et al. ...................... | 556/12 |
| 5,541,349 | 7/1996 | Wilson et al. ...................... | 556/10 |
| 5,817,849 | 10/1998 | Wilson et al. ...................... | 556/12 |

*Primary Examiner*—Porfirio Nazario-Gonzalez

[57] ABSTRACT

Catalytic derivatives of novel Group 4 metal complexes wherein the metal is in the +2, +3, or +4 formal oxidation state containing two ligand groups bound by π-electrons, at least one of which is a cyclic or noncyclic, non-aromatic, anionic, dienyl ligand group and having a bridged ligand structure, and the use thereof as catalysts for polymerizing addition polymerizable monomers are disclosed.

6 Claims, No Drawings

METAL COMPLEXES CONTAINING BRIDGED, NON-AROMATIC, ANIONIC, DIENYL GROUPS AND ADDITION POLYMERIZATION CATALYSTS THEREFROM

CROSS REFERENCE STATEMENT

This application is a Division of Ser. No. 08/896,898 filed Jul. 18, 1997 now U.S. Pat. No. 5,817,849 claims the benefit of U.S. Provisional Application No. 60/022,032, filed Jul. 22, 1996.

BACKGROUND OF THE INVENTION

This invention relates to certain Group 4 metal complexes comprising two ligand groups bonded to the metal by means of Π-electrons, at least one of which is a cyclic, or noncyclic, non-aromatic, anionic, dienyl group wherein the metal of said complexes is in the +2, +3, or +4 formal oxidation state and further wherein the two Π-bonded ligand groups are also bonded together via a divalent moiety. The invention also relates to techniques for preparing such complexes, catalyst systems comprising such complexes that are useful for polymerizing addition polymerizable monomers, and to such polymerization processes themselves.

Metal complexes containing delocalized, Π-bonded ligand groups and methods for their preparation are disclosed in U.S. application Ser. No. 545,403, filed Jul. 3,1990 (EP-A-416,815); U.S. application Ser. No. 547,718, filed Jul. 3, 1990 (EP-A-468,651); U.S. application Ser. No. 702,475, filed May 20, 1991 (EP-A-514,828); U.S. application Ser. No. 876,268, filed May 1, 1992, (EP-A-520,732) and U.S. application Ser. No. 8,003, filed Jan. 21, 1993 (WO93/19104), as well as U.S. Pat. No. 5,055,438, U.S. Pat. No. 5,057,475, U.S. Pat. No. 5,096,867, U.S. Pat. No. 5,064,802 and U.S. Pat. No. 5,132,380. The teachings of all the foregoing patents, publications and patent applications are hereby incorporated by reference.

In *Organometallics*, 10, 3643–3647, (1991) there were disclosed certain bridged 2,4-dimethylpentadienyl complexes of Ru and Yb. At page 3647 the authors speculated as to other applications for the ligand groups without mentioning any specific uses therefor.

Despite the advance in the art brought about by the foregoing metal complexes, new and improved catalytic compounds are still desired.

SUMMARY OF THE INVENTION

According to the present invention there are provided metal complexes corresponding to the formula (I):

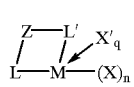
(I)

wherein:

M is a Group 4 metal in the +2, +3, or +4 formal oxidation state;

L is a group containing a divalent cyclic or noncyclic, non-aromatic, anionic, dienyl ligand group bound to M and Z, said L group containing up to 60 nonhydrogen atoms;

Z is a divalent moiety covalently bound to both L and L', comprising boron, or a member of Group 14 of the Periodic Table of the Elements, said moiety having up to 60 nonhydrogen atoms;

L' is L or an anionic, aromatic ligand group bonded to M via delocalized Π-electrons, said L' group having up to 60 nonhydrogen atoms;

X' independently each occurrence is a Lewis base containing up to 40 nonhydrogen atoms, and optionally X' and L or X' and L' are bonded together;

X independently each occurrence is a monovalent anionic moiety having up to 20 non-hydrogen atoms, provided however that neither X is an aromatic group that is Π-bonded to M; optionally, two X groups may be covalently bound together forming a divalent dianionic moiety having both valences bound to M; or two X groups together form a neutral, conjugated or nonconjugated diene that is Π-bonded to M (whereupon M is in the +2 oxidation state); or further optionally one or more X and one or more X' groups may be bonded together thereby forming a moiety that is both covalently bound to M and coordinated thereto by means of Lewis base functionality;

n is zero, one or two; and q is a number from 0 to 3.

Additionally according to the present invention there are provided processes for preparing such complexes comprising contacting a precursor Group 4 metal compound containing 2 displaceable ligand groups with a source of a dianionic ligand, $(L-Z-L')^{-2}$, optionally, if the precursor compound is in a lower formal oxidation state than the desired product, oxidizing the resulting complex, and optionally, if the precursor compound is in a higher formal oxidation state than the desired product, reducing the resulting complex.

Further according to the present invention there is provided a catalyst system useful for polymerization of addition polymerizable monomers comprising:

A) 1) one or more of the above metal complexes or the reaction product of the above described process, and 2) one or more activating cocatalysts;

or

B) the reaction product formed by converting one or more of the above metal complexes or the reaction product of the above described process to an active catalyst by use of an activating technique.

The present invention also provides a polymerization process comprising contacting one or more addition polymerizable monomers with a catalyst comprising one or more of the above catalyst systems. The polymerization may be performed under solution, suspension, slurry, or gas phase process conditions in a continuous or discontinuous process, and the composition or individual components thereof may be used in a heterogeneous, that is, a supported state, or in a homogeneous state. The catalyst can be used in combination with one or more additional catalysts of the same or different nature either simultaneously in the same or separate reactor or sequentially in the same or separate reactors.

Catalysts prepared from the complexes of the present invention are surprisingly active in the preparation of olefin polymers.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

Preferably, M is titanium, zirconium or hafnium, most preferably zirconium or titanium.

By the term "non-aromatic" when used with reference to L groups is meant that the atoms contributing electrons to the Π-system through which the anionic ligand is Π-bonded to the metal do not form a cyclic, planar, Π-system with 4p+2 electrons, where p is an integer greater than or equal to 0. Conversely, by the term "aromatic" is meant that the atoms contributing electrons to the Π-system through which the anionic ligand is Π-bonded to the metal form a cyclic, planar, Π-system with 4p+2 electrons, where p is an integer greater than or equal to 0. Examples of suitable L groups include divalent derivatives of pentadienyl-, cyclohexadienyl-, cyclosilahexadienyl-, cycloheptadienyl-, or cyclooctadienyl- groups, or inertly substituted derivatives thereof, as well as the diphenylmethyl group, that is:

Examples of aromatic ligand groups which are not included within the present definition of L include cyclopentadienyl ligands and substituted cyclopentadienyl ligands (including indenyl, fluorenyl, and hydrogenated derivatives thereof), boratabenzene and substituted boratabenzenes. L groups herein may be referred to as "dienyl" groups.

By the term "divalent derivatives" is meant that L and L' are bonded to both Z and M. Suitable inert substituents on L or L' include hydrogen, hydrocarbyl, halocarbyl, halohydrocarbyl, silyl, germyl, halo, amino, phosphino, cyano, hydrocarbyloxy, siloxy and combinations thereof, each of said inert substituents having up to 20 nonhydrogen atoms, or optionally, two or more such substituents (except hydrogen, cyano or halo) together form a ring structure, particularly a fused ring structure. Desirably, L or L' groups contain up to 50 non-hydrogen atoms. Cyclohexadienyl, dihydronaphthalenyl, hexahydronaphthalenyl, dihydroanthracenyl, hexahydroanthracenyl, decahydroanthracenyl groups and the foregoing inertly substituted derivatives thereof are specifically included within the above definition of L groups.

Examples of suitable L' groups include cyclopentadienyl ligands and substituted cyclopentadienyl ligands (including indenyl, fluorenyl, and hydrogenated derivatives thereof), boratabenzene and substituted boratabenzenes.

Preferred L groups correspond to the following formulas:

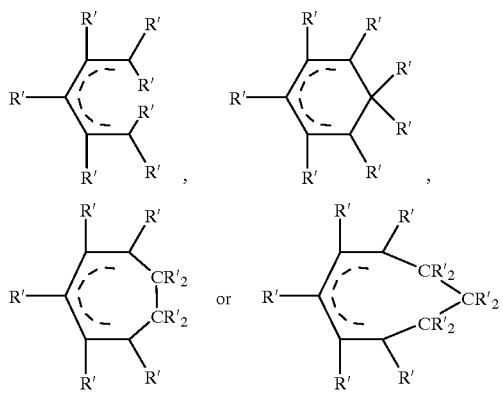

Preferred L' groups correspond to the above formula for L or to the following formulas:

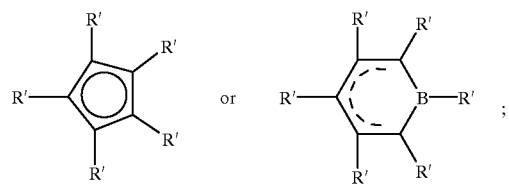

wherein R' in each occurrence is a moiety that is independently selected from the group consisting of hydrogen, hydrocarbyl, silyl, germyl, siloxy, amino, hydrocarbyloxy, cyano, halo and combinations thereof, said R' having up to 20 non-hydrogen atoms, and optionally, two or more R' groups (where R' is not hydrogen, halo or cyano) may together form a divalent derivative of one of the foregoing groups; and provided further that one R' comprises a covalent bond to Z.

Especially suitable L' groups are selected from the group consisting of divalent derivatives of pentadienyl, cyclohexadienyl, cyclosilahexadienyl, cycloheptadienyl; or cyclooctadienyl groups; hydrocarbyl, silyl, dihydrocarbylamino, hydrocarbyloxy and siloxy substituted derivatives of such groups; partially hydrogenated anthracenyl, or partially hydrogenated naphthalenyl groups; and hydrocarbyl, silyl, dihydrocarbylamino, hydrocarbyloxy or siloxy substituted derivatives of such partially hydrogenated anthracenyl or partially hydrogenated naphthalenyl groups.

The dienyl ligand group, L, is bound to the metal atom by any suitable electronic interaction. In certain circumstances the exact form of electronic interaction may be indeterminate, because several alternative isomeric configurations of the L ligand group may be generated, that is, $\eta^1$-$\eta^3$-, and $\eta^5$-bonded L ligands. This fact has been previously disclosed in the art, particularly in the teachings of R. D. Ernst, Chem. Rev., 88, 1255–1291 (1988), and R. D. Ernst, et al., J. Am. Chem. Soc. 107, 5016–5018 (1985). Moreover it is further well understood that the dienyl ligand in an $\eta^5$-bonded configuration may be depicted in several different isomeric configurations, known as the "W", "U" and "S" configurations. Such isomeric forms are illustrated with the 2,4-dimethylpentadien-3-yl ligand in the following drawing: Such variants are not necessarily separately named herein nor are the carbon atoms contributing to the dienyl ligand's bonds always identified since the equivalence of such L groups is well recognized by the skilled artisan, as illustrated by the above cited Ernst and Ernst, et al. references. It is to be further understood that in naming the foregoing L groups, the original positions of the double bonds of the dienyl ligand need not be identified since in the final delocalized ligand group the original double bonds no longer exist, i.e., the $\eta^5$-1,3-pentadien-3-yl group is identical to the $\eta^5$-1,4-pentadien-3-yl group. All such isomers are equivalent and may be referred to simply as $\eta^5$-pentadien-3-yl. For purposes of the present

"$\eta^1$"

"η3"

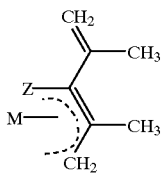

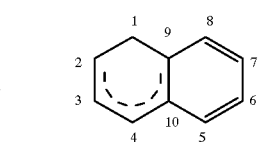

"η5-W"

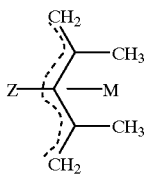

Hydrogenated positions of multicyclic systems are generally identified herein, however it is to be further understood that while various isomeric forms of such hydrogenated ligands are possible they are not necessarily named herein.

"η5-U"

Examples of the foregoing L groups include: ($\eta^5$-pentadien-1-yl), ($\eta^5$-pentadien-2-yl), ($\eta^5$-pentadien-3-yl), (2,4-dimethyl-$\eta^5$-pentadien-1-yl), (1,5-dimethyl-$\eta^5$-pentadien-2-yl), (2,4-dimethyl-$\eta^5$-pentadien-3-yl), (1,5-dimethyl-$\eta^5$-pentadien-3-yl), (1,5-bis(trimethylsilyl)-$\eta^5$-pentadien-3-yl), ($\eta^5$-cyclohexadien-1-yl), ($\eta^5$-cyclohexadien-2-yl), ($\eta^5$-cyclohexadien-3-yl), ($\eta^5$-cyclohexadien-6-yl), (6,6-dimethyl-$\eta^5$-cyclohexadien-1-yl), (6,6-dimethyl-$\eta^5$-cyclohexadien-2-yl), (6,6-dimethyl-$\eta^5$-cyclohexadien-3-yl), (6,6-dimethyl-$\eta^5$-cyclohexadien-6-yl), (6,6-dimethyl-$\eta^5$-6-sila-cyclohexadien-3-yl), (6,6-dimethyl-$\eta^5$-6-sila-cyclohexadien-6-yl), (6-t-butyl-6-methoxy-$\eta^5$-6-sila-cyclohexadien-3-yl), (6-methyl-6-fluoro-$\eta^5$-6-sila-cyclohexadien-3-yl), (1,2,6,6-tetramethyl-$\eta^5$-cyclohexadien-4-yl), (1,2,4,6,6-pentamethyl-$\eta^5$-cyclohexadien-3-yl), (1,2,4,6,6-pentamethyl-$\eta^5$-cyclohexadien-5-yl), (1,2,5,6,6-pentamethyl-$\eta^5$-cyclohexadien4yl), (1,2,4,5,6,6-hexamethyl-$\eta^5$-cyclohexadien-3-yl), (1,2,4,5-tetramethyl-6,6-cyclotrimethylene-$\eta^5$-cyclohexadien-3-yl), (2,3,4,9,10-$\eta$-1,2-dihydronaphthalen-1-yl), (2,3,4,9,10-$\eta$-1,2-dihydronaphthalen-2-yl), (1,1-dimethyl-2,3,4,9,10-$\eta$-1,2-dihydronaphthalen-2-yl), (1,1-dimethyl-2,3,4,9,10-$\eta$-1,2-dihydronaphthalen-4-yl), diphenylmethyl, di(1-cyclohexenyl)methyl, the equivalent ligands: (1,1-dimethyl-2,3,4,9,10-$\eta$-1,2,5,6,7,8-hexahydronaphthalen-4yl), (1,1-dimethyl-2,3,4,9,10-$\eta$-1,4,5,6,7,8-hexahydronaphthalen-4-yl), and (1,1-dimethyl-2,3,4,9,10-$\eta$-1,5,6,7,8,9-hexahydronaphthalen-4yl), the equivalent ligands (1,1,2,3-tetramethyl-2,3,4,9,10-$\eta$-1,2,5,6,7,8-hexahydronaphthalen-4yl), (1,1,2,3-tetramethyl-2,3,4,9,10-$\eta$-1,4,5,6,7,8-hexahydronaphthalen-4-yl), and (1,1,2,3-tetramethyl-2,3,4,9,10-$\eta$-5,6,7,8,9-hexahydronaphthalen-4-yl), (10,11,12,13,14-$\eta$-9,10-dihydroanthracen-9-yl), (10,11,12,13,14-$\eta$-9,10-dihydroanthracen-1-yl), (9,9-dimethyl-10,11,12,13,14-$\eta$-9,10-dihydroanthracen-10-yl), (10,11,12,13,14-$\eta$-1,2,3,4,9,10-hexahydroanthracen-9-yl), (10,11,12,13,14-$\eta$-1,2,3,4,9,10-hexahydroanthracen-1-yl), (10,11,12,13,14-$\eta$-1,2,3,4,9,11-hexahydroanthracen-9-yl), (10,11,12,13,14-$\eta$-1,4,5,8,9,10-hexahydroanthracen-1-yl), (9,9-dimethyl-10,11,12,13,14-$\eta$-1,4,5,8,9,10-hexahydroanthracen-10-yl), (9,9-dimethyl-10,11,12,13,14-$\eta$-1,4,5,8,9,10-hexahydroanthracen-2-yl), (8,8-dimethyl-5,6,7,13,14-$\eta$-1,4,5,8,9,10-hexahydroanthracen-10-yl), the equivalent ligands: (10,11,12,13,14-$\eta$-1,2,3,4,5,6,7,8,9,10-decahydroanthracen-9-yl) and (10,11,12,13,14-$\eta$-1,2,3,4,5,6,7,8,9,11-decahydroanthracen-9-yl); and the equivalent ligands: (9,9-dimethyl-10,11,12,13,14-$\eta$-1,2,3,4,5,6,7,8,9,10-decahydroanthracen-10-yl) and (9,9-dimethyl-10,11,12,13,14-$\eta$-1,2,3,4,5,6,7,8,9,11-decahydroanthracen-10-yl)

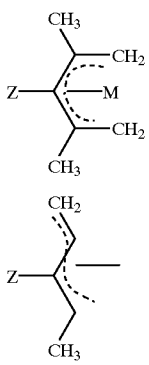

"η5-S"

invention it is to be understood that all possible isomeric forms of L are included in any reference to a specific isomer or electronic structure.

The positional numbering of the L group herein is accomplished by identifying the carbons contributing to the bonds to M and Z or where no ambiguity is possible, merely identifying the total carbons contributing to such bonds with the symbol, $\eta$. In monocyclic systems the lowest ordinals in sequence are assigned to the carbons contributing to the bonds with the positions otherwise numbered so as to produce the lowest positional numbers for substituted carbon atoms. Thus, the trimethyl-substituted cyclohexadienyl ligand group derived from 1,5,5-trimethyl-1,3-cyclohexadiene and bound at what was the the 2-position (illustrated as follows) is named (2,6,6-trimethyl-$\eta^5$-cyclohexadien-3-yl) rather than (4,6,6-trimethyl-$\eta^5$ cyclohexadien-3-yl) or (2,2,4-trimethyl-$\eta^5$-cyclohexadien-5-yl). The positional attachment of the Z group is indicated by identifying the carbon atom followed by -yl, i.e., ($\eta^5$-pentadien-1-yl) or ($\eta^5$-pentadien-2-yl). Multicyclic systems are numbered using standard

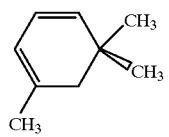 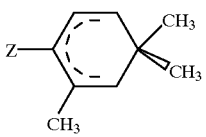

Cyclohexadiene compound      ligand nomenclature so as to avoid confusion. Specifically, hydrogenated naphthalenyl and hydrogenated anthracenyl systems are specifically illustrated as follows:

These groups are further illustrated in the following structures:

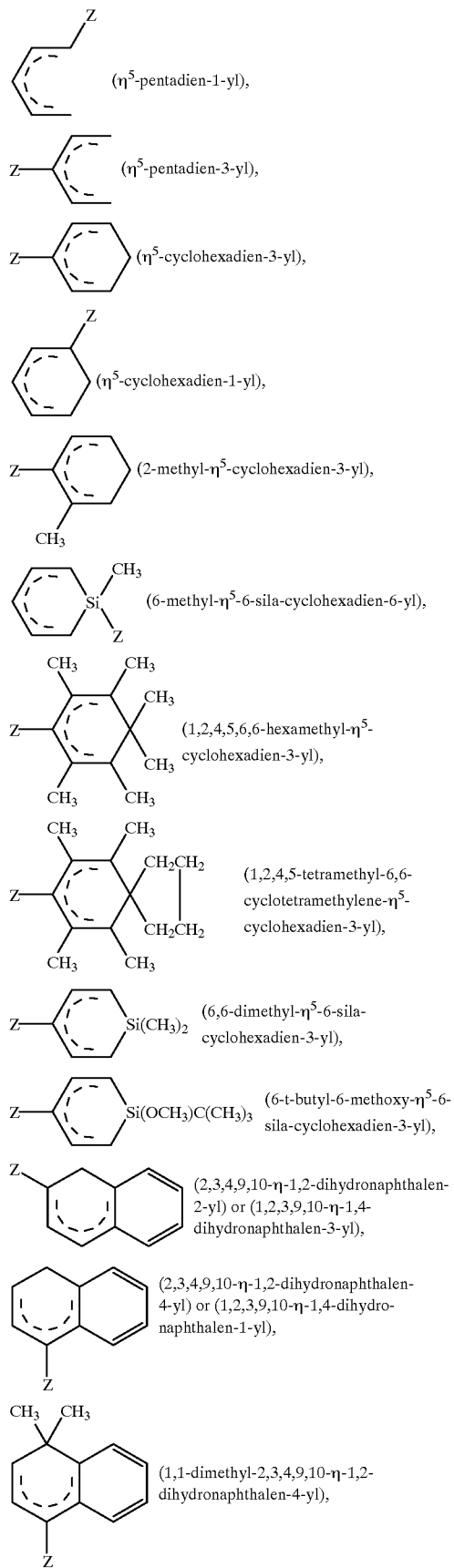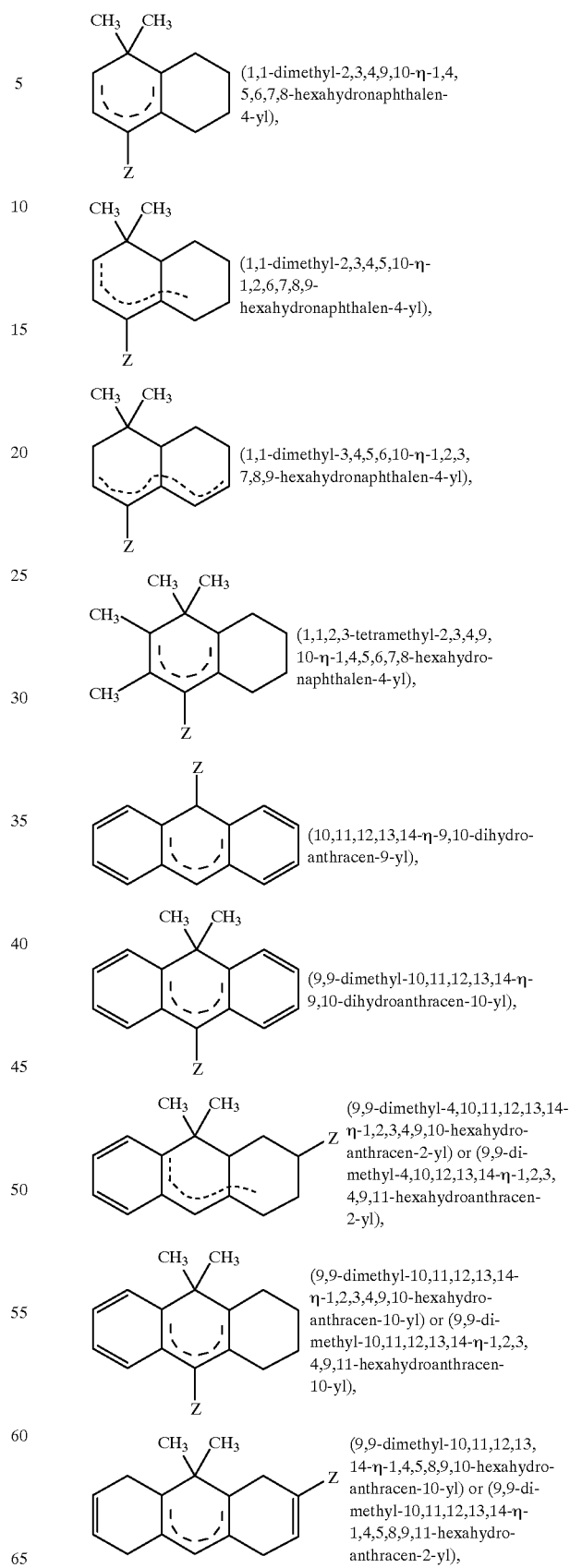

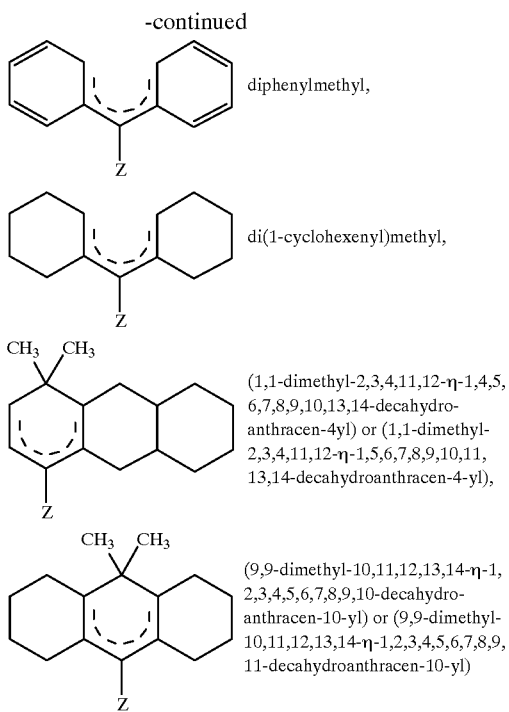

diphenylmethyl, di(1-cyclohexenyl)methyl, (1,1-dimethyl-2,3,4,11,12-η-1,4,5,
6,7,8,9,10,13,14-decahydro-
anthracen-4yl) or (1,1-dimethyl-
2,3,4,11,12-η-1,5,6,7,8,9,10,11,
13,14-decahydroanthracen-4-yl), (9,9-dimethyl-10,11,12,13,14-η-1,
2,3,4,5,6,7,8,9,10-decahydro-
anthracen-10-yl) or (9,9-dimethyl-
10,11,12,13,14-η-1,2,3,4,5,6,7,8,9,
11-decahydroanthracen-10-yl)

Preferred examples of X groups include: hydrocarbyl, carboxylate, sulfonate, hydrocarbyloxy, siloxy, amido, phosphido, sulfido, and silyl groups; as well as halo-, amino-, hydrocarbyloxy-, siloxy-, silyl-, and phosphino-substituted derivatives of such hydrocarbyl, carboxylate, sulfonate, hydrocarbyloxy, siloxy, amido, phosphido, sulfido, or silyl groups; hydride, halide and cyanide, said X group having up to 20 nonhydrogen atoms; or alternatively, two X groups together are a hydrocarbadiyl group, preferably a propane-1,3-diyl, butane-1,4-diyl, pentane-1,5-diyl, trimethylenemethane, 2-butene-1,4-diyl group, or a substituted derivative thereof wherein the substituent is independently each occurrence a hydrocarbyl or silyl group of up to 20 nonhydrogen atoms, said group forming a metallocycle, preferably a metallocyclopentene with M; or, further alternatively, two X groups together form a neutral, 1,4-disubstituted 1,3-butadiene (M being in the +2 formal oxidation state) wherein the substituent is independently each occurrence a hydrocarbyl or silyl group of up to 20 nonhydrogen atoms.

More preferred X groups are hydride, hydrocarbyl (including cyclohydrocarbyl), hydrocarbyloxy, amido (including pyridenyl), silyl, silylhydrocarbyl, siloxy, halide, aminobenzyl and aminomethylphenyl. Especially suited are hydride, chloride, methyl, neopentyl, benzyl, phenyl, methoxy, phenoxy, isopropoxy, butoxy, dimethylamido, 2-(N,N-dimethylamino)benzyl, 2-(N,N-dimethylaminomethylphenyl, allyl, methyl-substituted allyl (all isomers), pentadienyl, 2-methylpentadienyl, 3-methylpentadienyl, 2,4-dimethylpentadienyl, 6,6-dimethylcyclohexadienyl, trimethylsiloxy, and trimethylsilylmethyl.

Preferred X' groups include phosphines, phosphites, ethers, amines, carbon monoxide, salts of Group 1 or 2 metals, amine, aminohydrocarbyl or aminosilyl groups attached to L or L' and mixtures of the foregoing X' groups. Examples of the foregoing especially include trimethylphosphine, triethylphosphine, trifluorophosphine, triphenylphosphine, bis-1,2-(dimethylphosphino)ethane, trimethylphosphite, triethylphosphite, dimethylphenylphosphite, tetrahydrofuran, diethyl ether, carbon monoxide, pyridine, bipyridine, tetramethylethylenediamine (TMEDA), dimethoxyethane (DME), dioxane, triethylamine, lithium chloride, and magnesium chloride.

Further preferred metal coordination complexes according to the present invention correspond to the formula (II):

wherein:

Z is $SiR^*_2$, $CR^*_2$, $SiR^*_2SiR^*_2$, $CR^*_2CR^*_2$, $CR^*=CR^*$, $CR^*_2SiR^*_2$, $CR^*_2CR^*_2CR^*_2$, $CR^*_2SiR^*_2CR^*_2$, $SiR^*_2CR^*_2CR^*_2$, $SiR^*_2CR^*_2SiR^*_2$, $SiR^*_2SiR^*_2CR^*_2$, $SiR^*_2SiR^*_2SiR^*_2$, $SnR^*_2$, or $GeR^*_2$; wherein:

R* each occurrence is independently hydrogen, or a member selected from hydrocarbyl, silyl, hydrocarbyloxy, dihydrocarbylamino, siloxy, halogenated alkyl, halogenated aryl, and combinations thereof, said R* having up to 18 non-hydrogen atoms, and optionally (when R* is not hydrogen), two R* groups from Z, or an R* group from Z and an R' group from L or L' form a ring system.

M is titanium or zirconium in the +2, +3, or +4 formal oxidation state;

L is a divalent derivative of a pentadienyl, cyclohexadienyl, cyclosilahexadienyl, partially hydrogenated naphthalenyl, partially hydrogenated anthracenyl group or a hydrocarbyl or silyl substituted derivative of such cyclohexadienyl, cyclosilahexadienyl, partially hydrogenated naphthalenyl, partially hydrogenated anthracenyl group, each said hydrocarbyl or silyl substituent having up to 10 nonhydrogen atoms;

L' is L or a divalent derivative of a cyclopentadienyl, fluorenyl or indenyl group, a hydrocarbyl or silyl substituted derivative thereof, or a partially hydrogenated derivative thereof, such L' having up to 50 nonhydrogen atoms;

n is one or two, and when n is two, M is in the +4 formal oxidation state and X is halo, hydrocarbyl, or hydrocarbyloxy, said X having up to 12 non-hydrogen atoms, when n is one, M is in the +2 formal oxidation state and X is a neutral conjugated diene of from 5 to 30 carbons or M is in the +3 formal oxidation state and X is allyl, pentadienyl or N,N-dimethylaminobenzyl.

Most highly preferred metal coordination complexes are compounds corresponding to the formula (III):

wherein:

E is independently each occurrence silicon or carbon.

R" is independently each occurrence hydrogen or $C_{1-10}$ hydrocarbyl;

L' is cyclopentadienyl, indenyl or a $C_{1-20}$ hydrocarbyl substituted or multiply substituted derivative thereof;

M is titanium in the +4 formal oxidation state;

m is an integer from 1 to 3;

L is a (2,4-disubstituted pentadien-3-yl), (2,4-disubstituted pentadien-1-yl), (1,5-disubstituted pentadien-3-yl), (6,6disubstituted-$\eta^5$-cyclohexadien-3-yl), (6,6-disubstituted-$\eta^5$-cyclosilahexadien-3-yl), (1,2,3,4,5- pentasubstituted-η-cyclohexadien-6-yl), (1,2,3,4,5,6-hexasubstituted-η-cyclohexadien-6-yl), (1,2,4,5,6,6-hexasubstituted-$\eta^5$-cyclohexadien-3-yl)-, (1,1-disubstituted-$\eta^5$-hexahydronaphthalen4-yl), (1,1,2,3-tetrasubstituted-$\eta^5$-hexahydronaphthalen-4-yl), or (9,9-disubstituted-10,11,12,13,14-η-1,2,3,4,5,6,7,8,9,10-decahydroanthracene-10-yl), said substituents independently each occurrence being hydrocarbyl, hydrocarbyloxy, silyl, siloxy or a mixture thereof of up to 10 nonhydrogen atoms each; and X is methyl, phenyl, benzyl, trimethylsilylmethyl, chloro, methoxy, or ethoxy.

As a means of further illustration of the invention, specific metal complexes included therein are:

Pentadienyl and Substituted Pentadienyl Complexes ($\eta^5$-cyclopentadienyl)(2,4-dimethyl-$\eta^5$-pentadien-1-yl)dimethylsilane-zirconium(IV) dichloride; ($\eta^5$-cyclopentadienyl)(2,4-dimethyl-$\eta^5$-pentadien-3-yl)dimethylsilanezirconium(IV) dimethyl; ($\eta^5$-indenyl)(2,4-dimethyl-$\eta^5$-pentadien-3-yl) dimethysilanezirconium(IV) dimethyl; ($\eta^5$-2-methy-4-phenyl-indenyl)(2,4-dimethyl-$\eta^5$-pentadien-3-yl) dimethylsilanezirconium(IV) dimethyl; ($\eta^5$-tetrahydroindenyl)(2,4-dimethyl-$\eta^5$-pentadien-3-yl) dimethylsilanezirconium(IV) dimethyl; ($\eta^5$-fluorenyl)(2,4-dimethyl-$\eta^5$-pentadien-3-yl) dimethylsilanezirconium(IV) dimethyl; ($\eta^5$-octahydrofluorenyl)(2,4-dimethyl-$\eta^5$-pentadien-3-yl) dimethylsilanezirconium(IV) dimethyl; ($\eta^5$-cyclopentadienyl)(2,4-dimethyl-$\eta^5$-pentadien-3-yl) dimethylsilanezirconium(III) (N,N-dimethylaminobenzyl); ($\eta^5$-cyclopentadienyl)(2,4-dimethyl-$\eta^5$-pentadien-3-yl) methylphenylsilanetitanium (IV) dimethyl; 1-($\eta^5$-cyclopentadienyl)-2-(1,5-bis(trimethylsilyl)-2,4-dimethyl-$\eta^5$-pentadien-3-yl)-1,1,2,2-tetramethyldisilanezirconium (IV) dimethyl; bis(2,4-dimethyl-$\eta^5$-pentadien-1-yl)dimethylsilanezirconium (IV) dimethyl; ($\eta^5$-cyclopentadienyl)-(2,4-dimethyl-$\eta^5$-pentadien-1-yl)dimethylsilanetitanium (II) $\eta^4$-1,4-diphenyl-1,3-butadiene; ($\eta^5$-tetramethylcyclopentadienyl)(2,4-dimethyl-$\eta^5$-pentadien-1-yl)dimethylsilanetitanium(III) allyl; bis(2,4-dimethyl-$\eta^5$-pentadien-1-yl)dimethylsilanetitanium (IV) dibenzyl; (tetramethylcyclopentadienyl)(1,5-dimethyl-$\eta^5$-pentadien-3-yl)dimethylsilanetitanium (IV) methyl (trimethylsilylmethyl); ($\eta^5$-cyclopentadienyl)(2,4-dimethyl-$\eta^5$-pentadien-1-yl)dimethylsilanetitanium (IV) dimethoxy; 1-(tetramethylcyclopentadienyl)-2-(2,4-dimethyl-$\eta^5$-pentadien-3-yl)ethane-1,2-diylzirconium (IV) dimethyl; (cyclopentadienyl)(1,5-bis(trimethylsilyl)-$\eta^5$-pentadien-3-yl)dimethylsilanezirconium (IV) dimethyl; 1-tetramethylcyclopentadienyl-2-(4-methyl-$\eta^5$-pentadien-1-yl)ethane-1,2-diylzirconium(IV)dibenzyl, 1-(1-(N,N-diisopropylamino)-boratabenzene-2-(1,5-bis(trimethylsilyl)-2,4-dimethyl-$\eta^5$-pentadien-3-yl)-1,1,2,2-tetramethyldisilanezirconium (IV) dimethyl;

Cyclohexadienyl and Substituted Cyclohexadienyl Complexes ($\eta^5$-cyclopentadienyl)($\eta^5$-cyclohexadien-3-yl)dimethylsilanezirconium(IV) dichloride; ($\eta^5$-cyclopentadienyl)(6,6-dimethyl-$\eta^5$-cyclohexadien-3-yl)dimethylsilanezirconium(IV) dimethyl; ($\eta^5$-indenyl)(6,6-dimethyl-$\eta^5$-cyclohexadien-3-yl) dimethylsilanezirconium (IV) dimethyl; ($\eta^5$-tetrahydroindenyl)(6,6-dimethyl-$\eta^5$-cyclohexadien-3-yl) dimethylsilanezirconium(IV) dimethyl; ($\eta^5$-fluorenyl)(6,6-dimethyl-$\eta^5$-cyclohexadien-3-yl)dimethylsilanezirconium(IV) dimethyl; ($\eta^5$-octahydrofluorenyl)(6,6-dimethyl-$\eta^5$-cyclohexadien-3-yl)dimethylsilanezirconium(IV) dimethyl; ($\eta^5$-tetramethylcyclopentadienyl)($\eta^5$-cyclohexadien-3-yl)methylphenylsilanetitanium (IV) dimethyl; (1-(N,N-diisopropylamino)-boratabenzene)(6,6-dimethylcyclohexadien-3-yl)dimethylsilanezirconium(IV) dimethyl; ($\eta^5$-cyclopentadienyl)(6,6-dimethyl-$\eta^5$-cyclohexadien-3-yl)-1,1,2,2-tetramethyidisilanezirconium (IV) dimethyl; bis($\eta^5$-cyclohexadien-3-yl)dimethylsilanezirconium (IV) dimethyl; bis(6,6-dimethyl-$\eta^5$-cyclohexadien-3-yl)dimethylsilanezirconium (IV) dimethyl; ($\eta^5$-cyclopentadienyl)(2,3,4,9,10-$\eta^5$-1,2-dihydronaphthalen4-yl)dimethylsilanetitanium (II) $\eta^4$-1,4-diphenyl-1,3-butadiene;($\eta^5$-tetramethylcyclopentadienyl) (2,3,4,9,10-$\eta^5$-1,2-dihydronaphthalene4-yl)dimethylsilanetitanium(III) allyl; bis(9,9-dimethyl-10,11,12,13,14-$\eta^5$-1,2,3,4,9,10-hexahydroanthracen-10-yl)dimethylsilanetitanium (IV) dibenzyl; (tetramethylcyclopentadienyl)($\eta^5$-cyclohexadienyl)dimethylsilanetitanium (IV) methyl(trimethylsilylmethyl); bis($\eta^5$-cyclohexadienyl)dimethylsilanetitanium (IV) dimethoxy; 1-(tetramethylcyclopentadienyl)-2-(6,6-dimethyl-$\eta^5$-cyclohexadien-1-yl)-ethane-1,2diyl)zirconium (IV) dimethyl; (cyclopentadienyl)(6,6-dimethyl-$\eta^5$-cyclohexadien-1-yl)dimethylsilane-zirconium (IV) dimethyl; (tetramethylcyclopentadienyl)(6,6-dimethyl-$\eta^5$-cyclohexadien-1-yl)dimethylsilanezirconium (IV) dimethyl; and (tetramethylcyclopentadienyl)(6,6-dimethyl-$\eta^5$-cyclohexadien-1-yl)diisopropylsilanezirconium (IV) dimethyl.

Higher Cycloalkadienyl and Other Complexes ($\eta^5$-cyclopentadienyl)($\eta^5$-cycloheptadien-1-yl)dimethylsilanezirconium(IV) dichloride; ($\eta^5$-cycloheptadien-1-yl)(2,4-dimethyl-$\eta^5$-pentadien-3-yl) dimethylsilanezirconium (IV) dimethyl; ($\eta^5$-cyclopentadienyl)($\eta^5$-cyclooctadien-3-yl)methylphenylsilanetitanium (IV) dimethyl; 1-($\eta^5$-cyclopentadienyl)-2-(6,7,8-trimethyl-$\eta^5$-cyclooctadien-1-yl)-1,1,2,2-tetramethyidisilanezirconium (IV) dimethyl; bis($\eta^5$-cycloheptadien-3-yl)dimethylsilanezirconium (IV) dimethyl; ($\eta^5$-cyclopentadienyl)($\eta^5$-diphenylmethyl)dimethylsilanetitanium (II) $\eta^4$-1,4-diphenyl-1,3-butadiene; ($\eta^5$-tetramethylcyclopentadienyl)(6,6-dimethyl-$\eta^5$-cyclosilahexadien-3-yl)dimethylsilanetitanium(III) allyl; bis (2,4-dimethyl-$\eta^5$cycloheptadien-3-yl)dimethylsilanetitanium (IV) dibenzyl; (tetramethylcyclopentadienyl)(1,5-dimethyl-$\eta^5$-cyclooctadien-3-yl)dimethylsilanetitanium (IV) methyl (trimethylsilylmethyl); ($\eta^5$-cyclopentadienyl)($\eta^5$-cycloheptadien-1-yl)dimethylsilanetitanium (IV) dimethoxy; 1-(tetramethylcyclopentadienyl)-2-(6,7,8-trimethyl-$\eta^5$-cyclooctadien-1-yl)ethane-1,2-diylzirconium (IV) dimethyl; and (cyclopentadienyl)(6,7,8-trimethyl-$\eta^5$-cyclooctadien-1-yl)dimethylsilanezirconium (IV) dimethyl.

The skilled artisan will recognize that additional members of the foregoing list will include the corresponding titanium, zirconium or hafnium containing derivatives, as well as complexes that are variously substituted as herein defined.

The complexes can be prepared in one embodiment by combining a precursor metal compound corresponding to the formula $M(X)_4X'_q$, wherein M, X, X' and q are as previously defined with respect to formula (I), with the added proviso that X in two occurrences is a monovalent anionic moiety having up to 20 non-hydrogen atoms capable of displacement by a dianion ligand, $(L-Z-L')^{-2}$, wherein L, Z, and L' are as previously defined with respect to formula (I), with a reactant corresponding to the formula: $W_2$ (L-Z-L')$^{-2}$, wherein W independently each occurrence is a Group 1 or Group 2 metal, a Grignard, hydride or a $C_{1-4}$trialkylsilyl group. The reaction may optionally be performed in the presence of a reducing agent or in the presence of a Lewis base, X'. The reaction is preferably conducted in an inert, organic, liquid at a temperature from –100 to 300° C., preferably from –78 to 150° C., most preferably from 0 to 125° C. and optionally recovering the complex. Preferred reactants especially include lithium, sodium, potassium, magnesium, or Grignard derivatives of the dianion ligand. Suitable trialkylsilyl derivatives especially include trimethylsilyl derivatives of the dianion ligand. Suitable reducing agents especially include n-butyl lithium, lithium or magnesium.

In a preferred embodiment, the complexes wherein M is in the +4 formal oxidation state can be prepared by contacting a precursor metal compound wherein the metal is in the +3 formal oxidation state, corresponding to the formula: $M(X)_3X'_q$, wherein M, X, X' and q are as previously defined, with the proviso that X in two occurrences is a monovalent anionic moiety having up to 20 non-hydrogen atoms capable of displacement by a dianion ligand, (L-Z-L')$^{-2}$, wherein L, Z, and L' are as previously defined, with the above sources of the dianionic ligand, (L-Z-L')$^{-2}$; and thereafter or concurrently oxidizing the metal center with an organic halogen-containing oxidizing agent, or a metal halide oxidizing agent. Particularly preferred oxidizing agents are methyl chloride, methylene chloride, chloroform, carbon tetrachloride, $PbCl_2$ and AgCl.

The dianionic group is prepared using standard synthetic measures known to the skilled artisan or by use of procedures analogous to known routes. The moieties containing cyclosilahexadienyl functionality are prepared in a manner analogous to the techniques disclosed in Jutzi, et al, *Chem. Ber.*, 117, 1885–95 (1984); *J. Am. Chem. Soc.*, 103 6788–6789 (1981); and *Zh. Oshch. Khim.*, 44,226–227 (1979), modified according to EP-A-563,365 as to the particular silane moiety utilized.

Suitable reaction media for the formation of the complexes are aliphatic and aromatic hydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, xylene, and styrene, alkyl ethers having from 1 to 4, carbons in each alkyl group; $C_{1-4}$ dialkyl ether derivatives of (poly)alkylene glycols, and tetrahydrofuran. Mixtures of the foregoing are also suitable. Preferred solvents include $C_{5-10}$ alkanes, dialkyl ethers having from 1 to 4 carbons in each alkyl group, tetrahydrofuran, toluene, and mixtures thereof. Solvated adducts of the metal precursor complex may also be used if desired. Examples of solvated adducts include pyridine-, diethylether-, tetrahydrofuran- (THF), 1,2-dimethoxyethane-(DME), or tetramethyl-ethylenediamine-(TMEDA) containing adducts.

The complexes according to the present invention are surprisingly stable and readily synthesized. They are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; Lewis acids, such as $C_{1-45}$ hydrocarbyl substituted Group 13 compounds, especially tri(hydrocarbyl)aluminum- or tri(hydrocarbyl)boron compounds and halogenated (including perhalogenated) derivatives thereof, having from 1 to 20 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, EP-A468,651 (equivalent to U.S. Ser. No. 07/547,718), EP-A-520,732 (equivalent to U.S. Ser. No. 07/876,268), and EP-A-640,090 (equivalent to U.S. Ser. No. 07/884,966 filed May 1, 1992), the teachings of which are hereby incorporated by reference.

Combinations of Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane and tris(o-nonafluorobiphenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts.

Suitable ion forming compounds useful as cocatalysts in one embodiment of the present invention comprise a cation which is a Bronsted acid capable of donating a proton, and a compatible, noncoordinating anion, A$^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*-H)_d^+(A^{d-})$$

wherein:
L* is a neutral Lewis base;
(L*−H)+ is a Bronsted acid;
$A^{d-}$ is a noncoordinating, compatible anion having a charge of d−, and
d is an integer from 1 to 3.

More preferably $A^{d-}$ corresponds to the formula: $[M'^{k+}Q_{n'}]^{d-}$
wherein:
k is an integer from 1 to 3;
n' is an integer from 2 to 6;
n'−k=d;
M' is an element selected from Group 13 of the Periodic Table of the Elements; and
Q independently each occurrence is selected from hydride, dialkylamido, halide, hydrocarbyl, hydrocarbyloxide, halosubstituted-hydrocarbyl, halosubstituted hydrocarbyloxy, and halo- substituted silylhydrocarbyl radicals (including perhalogenated hydrocarbylperhalogenated hydrocarbyloxy- and perhalogenated silylhydrocarbyl radicals), said Q having up to 20 carbons with the proviso that in not more than one occurrence is Q halide. Examples of suitable hydrocarbytoxide Q groups are disclosed in U.S. Pat. No. 5,296,433, the teachings of which are herein incorporated by reference.

In a more preferred embodiment, d is one, that is, the counter ion has a single negative charge and is A−. Activating cocatalysts comprising boron which are particularly useful in the preparation of catalysts of this invention may be represented by the following general formula:

$$[L^*-H]^+[BQ_4]^-$$

wherein:
L* is as previously defined;
B is boron in a valence state of 3; and
Q is a hydrocarbyl-, hydrocarbyloxy-, fluorinated hydrocarbyl-, fluorinated hydrocarbyloxy-, or fluorinated silylhydrocarbyl group of up to 20 nonhydrogen atoms, with the proviso that in not more than one occasion is Q hydrocarbyl.

Most preferably, Q is each occurrence a fluorinated aryl group, especially, a pentafluorophenyl or nonafluorobiphenyl group.

Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butylammonium tetraphenylborate, tri(t-butyl) ammonium tetraphenylborate, N,N-dimethylanilinium tetraphenylborate, N,N-diethylanilinium tetraphenylborate, N,N-dimethyl-2,4,6-trimethylanilinium tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(sec-butyl)ammonium tetrakis(pentafluorophenyl) borate, N,N-dimethylanilinium tetrakis(pentafluorophenyl) borate, N,N-dimethylanilinium n-butyltris(pentafluorophenyl) borate, N,N-dimethylanilinium benzyltris (pentafluorophenyl) borate, N,N-dimethylanilinium tetrakis (4(t-butyldimethylsilyl)-2,3,5,6-tetrafluorophenyl) borate, N,N-dimethylanilinium tetrakis(4-(triisopropylsilyl)-2,3,5, 6-tetrafluorophenyl) borate, N,N-dimethyl-N-octadecylammonium tetrakis(pentafluorophenyl)borate. N,N-dioctadecyl-N-methylammonium tetrakis (pentafluorophenyl)borate. N,N-dimethyl-N-octadecylammonium tetrakis(nonafluorobiphenyl)borate, N,N-dimethylanilinium pentafluorophenoxytris (pentafluorophenyl) borate, N,N-diethylanilinium tetrakis (pentafluorophenyl) borate, N,N-dimethyl-2,4,6-trimethylanilinium tetrakis(pentafluorophenyl) borate, trimethylammonium tetrakis(2,3,4,6-tetrafluorophenyl) borate, triethylammonium tetrakis(2,3,4,6-tetrafluorophenyl) borate, tripropylammonium tetrakis(2,3, 4,6-tetrafluorophenyl) borate, tri(n-butyl)ammonium tetrakis(2,3,4,6-tetrafluorophenyl) borate, dimethyl(t-butyl) ammonium tetrakis(2,3,4,6-tetrafluorophenyl) borate, N,N-dimethylanilinium tetrakis(2,3,4,6tetrafluorophenyl) borate, N,N-diethylanilinium tetrakis(2,3,4,6-tetrafluorophenyl) borate, and N,N-dimethyl-2,4,6-trimethylanilinium tetrakis (2,3,4,6-tetrafluorophenyl) borate; dialkyl ammonium salts such as: di-(i-propyl)ammonium tetrakis(pentafluorophenyl) borate, and dicyclohexylammonium tetrakis (pentafluorophenyl) borate; tri-substituted phosphonium salts such as: triphenylphosphonium tetrakis (pentafluorophenyl) borate, tri(o-tolyl)phosphonium tetrakis (pentafluorophenyl) borate, and tri(2,6-dimethylphenyl) phosphonium tetrakis(pentafluorophenyl) borate; di-substituted oxonium salts such as: diphenyloxonium tetrakis(pentafluorophenyl) borate, di(o-tolyl)oxonium tetrakis(pentafluorophenyl) borate, and di(2,6-dimethylphenyl)oxonium tetrakis(pentafluorophenyl) borate; di-substituted sulfonium salts such as: diphenylsulfonium tetrakis(pentafluorophenyl) borate, di(o-tolyl) sulfonium tetrakis(pentafluorophenyl) borate, and di(2,6-dimethylphenyl)sulfonium tetrakis(pentafluorophenyl) borate.

Preferred [L*−H]+ cations are N,N-dimethylanilinium, triethylammonium, methyldioctadecylammonium, dimethyloctadecylammonium and tributylammonium.

Another suitable ion forming, activating cocatalyst comprises a salt of a cationic oxidizing agent and a noncoordinating, compatible anion represented by the formula:

$$(OX^{e+})_d(A^{d-})_e$$

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, Ag+, or Pb+2. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion and a noncoordinating, compatible anion represented by the formula:

$$©+A^-$$

wherein:
©+ is a $C_{1-20}$ carbenium ion; and
A− is as previously defined. A preferred carbenium ion is the trityl cation, i.e. triphenylmethylium.

A further suitable ion forming, activating cocatalyst comprises a compound which is a salt of a silylium ion and a noncoordinating, compatible anion represented by the formula:

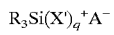

$R_3Si(X')_q^+A^-$ wherein:

R is $C_{1-10}$ hydrocarbyl, and X', q and $A^-$ are as previously defined.

Preferred silylium salt activating cocatalysts are trimethylsilylium tetrakis(pentafluorophenyl)borate, triethylsilylium tetrakis(pentafluorophenyl)borate and ether substituted adducts thereof. Silylium salts have been previously generically disclosed in *J. Chem Soc. Chem.Comm.*, 1993, 383–384, as well as Lambert, J. B., et al., *Organometallics*, 1994, 13, 2430–2443. The use of the above silylium salts as activating cocatalysts for addition polymerization catalysts is disclosed and claimed in U.S. Pat. No. 5,625,084, issued Apr. 29, 1997.

Certain complexes of alcohols, mercaptans, silanols, and oximes with tris(pentafluorophenyl)borane are also effective catalyst activators and may be used according to the present invention. Such cocatalysts are disclosed in U.S. Pat No. 5,296,433, the teachings of which are herein incorporated by reference.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), dimethoxyethane (DME), and mixtures thereof.

The electrolysis may be conducted in a standard electrolytic cell containing an anode and cathode (also referred to as the working electrode and counter electrode respectively). Suitable materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in is the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and a compatible, noncoordinating anion, $A^-$. Preferred supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include tetrahydrocarbyl substituted ammonium or phosphonium cations having up to 40 nonhydrogen atoms. Preferred cations are the tetra-n-butylammonium- and tetraethylammonium- cations.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoroaryl) borates having from 1 to 10 carbons in each hydrocarbyl or perfluoroaryl group, especially tetra-n-butylammonium tetrakis(pentafluorophenyl) borate,or tetra-n-butylammonium tetrakis(nonafluorobiphenyl) borate.

A further recently discovered electrochemical technique for generation of activating cocatalysts is the electrolysis of a disilane compound in the presence of a source of a noncoordinating compatible anion. This technique is more fully disclosed and claimed in U.S. Pat. No. 5,372,682.

The foregoing activating techniques and ion forming cocatalysts are also preferably used in combination with a tri(hydrocarbyl)aluminum or tri(hydrocarbyl)borane compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:10 to 1:1. In a particularly preferred embodiment of the invention the cocatalyst can be used in combination with a tri (hydrocarbyl)aluminum compound having from 1 to 10 carbons in each hydrocarbyl group or an oligomeric or polymeric alumoxane. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 2 to 6 carbons in each alkyl group, especially those wherein the alkyl groups are methyl, ethyl, propyl, isopropyl, n-butyl, isobutyl, pentyl, neopentyl, or isopentyl, and methylalumoxane, modified methylalumoxane (that is, methylalumoxane modified by reaction with triisobutyl aluminum) (MMAO) and isobutylalumoxane. The molar ratio of metal complex to aluminum compound is preferably from 1: 10,000 to 100:1, more preferably from 1:1000 to 10:1, most preferably from 1: 500 to 1:1. A most preferred activating cocatalyst comprises both a Lewis acid and an alumoxane, especially tris(pentafluorophenyl)borane or tris (nonafluoro-biphenyl)borane and methylalumoxane, modified methylalumoxane, or diisobutylalumoxane.

Upon activation of the metal complexes containing two distinct X groups, utilizing one of the preceding cation forming activating cocatalysts or activating techniques, there is believed to be formed, without wishing to be bound by such belief, a cationic metal complex corresponding to the formula:

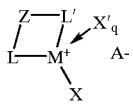

wherein:

M is a Group 4 metal in the +4 formal oxidation state, and L, Z, L', X', X, and q are as previously defined, and A- is as previously defined and is the noncoordinating anion from the activating cocatalyst or is formed concurrently by the activating technique.

Utilizing the preferred neutral Lewis acid activating cocatalyst, $B(C_6F_5)_3$, A- of the foregoing cationic metal complexes is believed to correspond to the formula: $XB(C_6F_5)_3^-$, wherein X is a $C_{1-10}$ hydrocarbyl group. Most preferably A- is $B(C_6F_5)_4^-$ or $XB(C_6F_5)_3^-$, wherein X is a $C_{1-10}$ hydrocarbyl group.

It is further believed, without wishing to be bound by such belief, that Group 4 metal complexes in the +4 oxidation state, wherein two X groups together with the metal M form a metallacycle, uniquely form novel zwitterionic complexes upon activation by combination with the previously mentioned neutral Lewis acid activating cocatalysts. Such zwitterionic metal complexes are believed correspond to the formula: wherein:

M is a Group 4 metal in the +4 oxidation state;
L, Z, L', are as previously defined;

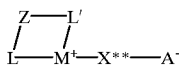

X** is the divalent remnant formed by ring opening at one of the carbon to metal bonds of the metallacycle formed by M and two X groups taken together; and —A— is a ligand moiety derived from the anion, A-.

Such zwitterionic complexes preferably correspond to one of the two equilibrium structures of the formula:

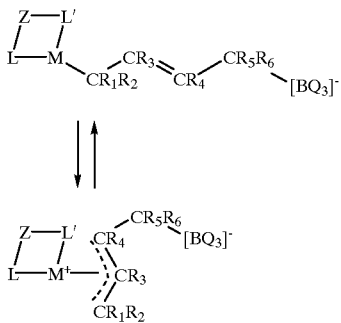

wherein:

M is titanium or zirconium;

L, Z. and L' are as previously defined;

$R_1$, $R_2$, $R_3$, $R_4$, $R_5$, and $R_6$ are independently each occurrence hydrogen or a hydrocarbyl or silyl group having from 1 to 20 nonhydrogen atoms;

B is boron in a valence state of 3, and

Q is as previously defined.

The catalysts may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain, macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,5-hexadiene, 1,7-octadiene, vinylcyclohexane, 4-vinylcyclohexene, allylbenzene, divinylbenzene, 2,5-norbornadiene and mixtures of such other preferred monomers with $C_{2-20}$ α-olefins.

In general, the polymerization may be accomplished at conditions well known in the prior art for Ziegler-Natta or Kaminsky-Sinn type polymerization reactions, that is, temperatures from −100–250° C. and pressures from 0.0001 to 1000 MPa. Suspension, solution, slurry, gas phase, bulk or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase or slurry polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$: 1 to $10^{-1}$:1, more preferably from $10^{-12}$: 1 to $10^{-5}$: 1.

Suitable solvents or diluents for polymerization are noncoordinating, inert liquids. Examples include $C_{4-10}$ straight and branched-chain hydrocarbons, especially butane, isobutane, pentane, isopentane, hexane, heptane, octane, and mixtures thereof; cyclic and alicyclic hydrocarbons such as cyclopentane, cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene (all isomers). Suitable solvents also include liquid olefins or other monomers or mixtures thereof as previously mentioned.

The catalysts may also be utilized in combination with at least one additional homogeneous or heterogeneous polymerization catalyst in the same or separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993, the teachings of which are hereby incorporated by reference herein.

One such polymerization process comprises:

contacting, optionally in a solvent, one or more α-olefins with a catalyst according to the present invention comprising one or more metal complexes according to the present invention in one or more continuous stirred tank or tubular reactors, or in the absence of solvent, optionally in one or more stirred bed or fluidized bed gas phase reactors, connected in series or in parallel, and recovering the resulting polymer.

In another such polymerization process, in one or more of the foregoing reactors, one or more α-olefins are also contacted with one or more catalyst compositions comprising one or more metal complexes according to the present invention in admixture with a catalyst composition comprising one or more homogeneous metallocene complexes other than a complex according to the present invention, said catalyst composition also comprising one or more cocatalyst activators.

In yet another process an ethylene/α-olefin interpolymer composition is prepared by:

(A) contacting ethylene and at least one other α-olefin under polymerization conditions in the presence of a homogeneous catalyst composition of the present invention comprising a metal complex of the present invention with at least one of the aforementioned activating cocatalysts in at least one reactor to produce a first interpolymer or optionally a solution of a first interpolymer, (B) contacting ethylene and at least one other α-olefin under polymerization conditions at optionally a different, preferably a higher, polymerization reaction temperature than used in step (A) in the presence of a heterogeneous Ziegler catalyst in at least one other reactor to produce a second interpolymer optionally in solution, and (C) combining the first interpolymer and second interpolymer to form an ethylene/α-olefin interpolymer blend composition, and (D) recovering the ethylene/α-olefin interpolymer blend composition.

Preferably the heterogeneous Ziegler catalyst comprises:
  (i) a solid support component comprising magnesium halide, silica, modified silica, alumina, aluminum phosphate, or a mixture thereof, and
  (ii) a transition metal component represented by the formula:

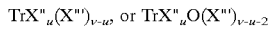

wherein:
Tr is a Group 4, 5, or 6 metal,
O is oxygen,
X" is halogen,
X'" is independently selected from hydrocarbyl, silyl, hydrocarbyloxy or siloxy having up to 10 non-hydrogen atoms,
u is a number from 0 to 6 that is less than or equal to v, and
v is the formal oxidation number of Tr.

These polymerizations are generally carried out under solution conditions to facilitate the intimate mixing of the two polymer-containing streams. The foregoing technique allows for the preparation of ethylene/α-olefin interpolymer compositions having a broad range of molecular weight distributions and composition distributions. Preferably, the heterogeneous catalyst is also chosen from those catalysts which are capable of efficiently producing the polymers under high temperatures, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a solution process under suitable solution polymerization temperatures and pressures in at least one reactor containing a catalyst composition comprising the metal complex of the present invention with at least one of the aforementioned activating cocatalysts to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition Preferably the heterogeneous Ziegler catalyst comprises:
  (i) a solid support component comprising a magnesium halide, silica or modified silica, including calcined silica, and
  (ii) a transition metal component represented by the formula:

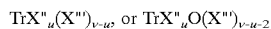

wherein:
Tr, X", X'", O, u, and v are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{3-8}$ α-olefins, most desirably 1-octene.

The skilled artisan will appreciate that the invention disclosed herein may be practiced in the absence of any component which has not been specifically disclosed.

EXAMPLES

Example 1
1,2-(bis-(4,4-dimethyl-2,5-cyclohexadienyl)-1,1 ,2,2-tetramethyldisilane) zirconium dichloride To 5.50 grams, 16.6 mmol, of 1,2-bis-(4,4-dimethyl-2,5-cyclohexadienyl)-1,1,2,2-tetramethyidisilane in 25 mL of tetrahydrofuran (THF) at about 25° C. was added 24.3 mL of a 1.37 M hexane solution of t-butyl lithium (33.3 mmol). Vigorous bubbling occurred and the color changed to a deep reddish-brown. The reaction mixture was allowed to stir for 6 hours at about 25° C., whereupon about 180 mL of additional toluene was added followed by 3.88 grams of zirconium tetrachloride (16.6 mmol). The resulting reaction mixture was allowed to stir for approximately 16 hours at about 25° C. The solvent was removed under reduced pressure from the deep reddish-brown solution. The residue was extracted with toluene and filtered and the solvent was again removed under reduced pressure. The residue was again extracted with hexane and filtered. The dark brown filtrate was dried under reduced pressure, giving the desired product.

Example 2
(Tetramethylcyclopentadienyl)(cylcooctadienyl) dimethylsilanezirconium dichloride
(tetramethylcyclopentadienyl)dimethylsilyl (cyclooctadiene)

Potassium cyclooctadienide (3.42 g, 23.4 mmols) dissolved in about 50 mL of THF was added to a solution of (tetramethylcyclopentadienyl)chloro-dimethylsilane (5.02 g, 23.4 mmols) in about 80 mL of THF at about 25° C. A precipitate formed and the reaction mixture was stirred for about 16 hours at about 25° C., after which time the reaction mixture was filtered and the solvents removed under reduced pressure. The residue was extracted with hexane and filtered. The solvents were again removed under reduced pressure leaving the desired isomeric product comprising (tetramethylcyclopentadienyl)(cylcoocta-2,7-dien-1-yl)

dimethylsilane and (tetramethylcyclopentadienyl) (cylcoocta-2,4-dien-1-yl)dimethylsilane.

Dipotassium (tetramethylcyclopentadienyl) (cylcooctadienyl)dimethylsilane

About 200 mL of hexane was added to the residue produced in the foregoing step followed by 5.90 g, 46.7 mmol, of potassium t-butoxide in about 28 mL cyclohexane. To this solution was then added 32.8 mL, 46.8 mmol, of a 1.43 M hexane solution of n-butyllithium at about 25° C. A yellow-orange precipitate formed. The reaction mixture was stirred for several hours at about 25° C., after which time it was filtered. The solid was washed with hexane several times and dried under reduced pressure.

(Tetramethylcyclopentadienyl)(cyclooctadienyl) dimethylsilanezirconium dichloride Dipotassium (tetramethylcyclopentadienyl) (cylcooctadienyl)dimethylsilane (3.00 g, 8.27 mmols) was combined with zirconium tetrachloride (1.93 g, 8.27 mmols) in about 150 mL toluene at about 25° C., to form a red solution and undissolved brown solids. The reaction mixture was stirred about 16 hours at about 25° C., and then filtered to give an orange red solution and a brown solid. The solution was dried under reduced pressure, and the resulting solid washed with hexane, refiltered, rewashed with hexane, and dried again to give the desired product, (tetramethylcyclopentadienyl)(cyclooctadienyl) dimethylsilanezirconium dichloride, as a mixture of the 1,7-cyclooctadien-1-yl and 1-4-cyclooctadien-1-yl isomers.

Example 3

(Tetramethylcyclopentadienyl)(diphenylmethyl) dimethylsilanezirconium dichloride Preparation of (tetramethylcyclopentadienyl) (diphenylmethyl)dimethylsilane Potassium diphenylmethanite (4.91 g, 23.8 mmol) was slowly added to (tetramethylcyclopentadienyl) dimethylsilylchloride (5.11 g, 23.8 mmol) dissolved in about 65 mL of THF at about 25° C. A precipitate formed and the reaction mixture was stirred about 16 hours more at about 25° C. after which time the reaction mixture was filtered, the solvent was removed under reduced pressure and the residue was extracted with hexane and filtered. The solvent was removed under reduced pressure to give the desired product.

Preparation of (tetramethylcyclopentadienyl) (diphenylmethyl)dimethylsilane dipotassium salt To the product resulting from the above procedure was added about 200 mL of hexane followed by 6.01 grams, 47.6 mmol, of potassium t-butoxide in about 29 mL hexane and 47.8 mmol of n-butyllithium in about 33 mL of hexane at about 25° C. A bright red-orange precipitate formed The reaction mixture was stirred several hours then filtered, washed with hexane several times and then dried under vacuum.

Preparation of (tetramethylcyclopentadienyl) (diphenylmethyl)dimethylsilane-zirconium dichloride (Tetramethylcyclopentadienyl)(diphenylmethyl) dimethylsilane dipotassium salt (3.00 g, 7.10 mmol) was combined with 1.654 grams of zirconium tetrachloride in 150 mL of toluene at about 25° C. The reaction mixture was stirred overnight at about 25° C., and then filtered. The solvent was removed under vacuum. The residue was washed with hexane and filtered, washed again with hexane and dried to give the desired product as a red-orange solid.

Example 4

2-(Cyclopentadienyl)-2-(cyclooctadienyl)propanezirconium dichloride

Preparation of 2-(cyclopentadienyl)-2-(cyclooctadienyl) propane dipotassium salt To 2.50 grams, 23.6 mmols of 6,6-dimethylfulvene in about 100 mL of THF was added 3.45 grams, 23.6 mmols, of potassium cyclooctadienide dissolved in about 70 mL of THF. The reaction mixture turned red and was stirred for about 16 hours at 25° C. after which time the solvent was removed under reduced pressure to give a sticky, oily solid. About 200 mL of hexane was added to the solution followed by potassium t-butoxide (2.98 g, 23.6 mmols) in about 14 mL of cyclohexane, and butyllithium (23.6 mmols) in about 16 mL of hexane. A brown precipitate formed. The mixture was stirred at about 25° C. for several hours and then filtered. The solid product was washed several times with hexane and dried under reduced pressure to give the product as dipotassium 2-(cyclooctadienyl)-2-(cyclopentadienyl) propane in both the cycloocta-2,7-dien-1 -yl and cycloocta-2,4dien-1-yl isomeric forms.

Preparation of 2-(cyclopentadienyl)-2-(cyclooctadienyl) propanezirconium dichloride 2-(Cyclopentadienyl)-2-(cyclooctadienyl)propane dipotassium salt (3.00 g, 10.3 mmol) was slowly added to zirconium tetrachloride (2.41 g, 10.3 mmol) in about 150 mL of toluene at about 25° C. The reaction mixture was allowed to stir overnight at about 25° C. The resulting mixture was filtered and the toluene was removed under reduced pressure. The resulting green solid was extracted with hexane, filtered, and dried to give the desired product as a green solid.

Example 5

3-(Cyclopentadienyl)3-(diphenylmethyl)propanezirconium dichloride

Preparation of 2-(cyclopentadienyl)-2,2-dimethyl-1,1-diphenylethane

Potassium diphenylmethanide (5.72 g, 27.8 mmols) in about 50 mL of THF was slowly added to 6,6-dimethylfulvene (2.94 g, 27.8 mmols) in about 100 mL of THF at about 25 C. The reaction mixture was stirred at about 25° C. for about 16 hours. The solvent was removed under reduced pressure to give the desired product as a sticky, oily solid.

Preparation of 2-(cyclopentadienyl)-2,2-dimethyl-1,1-diphenylethane dipotassium salt The above prepared solid was dissolved in about 200 mL of hexane. Potassium t-butoxide (3.50 g, 27,7 mmols) in about 16 mL cyclohexane was then added followed by 19.5 mL of a 1.43 M hexane solution of n-butyllithium (27.7 mmoles). The reaction mixture was stirred for several hours at 25° C., then filtered and washed with hexane several times and dried under reduced pressure to give the desired product.

Preparation of 3-(Cyclopentadienyl)-3-(diphenylmethyl) propanezirconium dichloride 2-(Cyclopentadienyl)-2,2-dimethyl-1,1-diphenylethane dipotassium salt (3.00 g, 8.56 mmol) in about 50 mL THF was added to zirconium tetrachloride (1.99 g, 8.56 mmols) in about 100 mL of THF. The reaction mixture was stirred overnight at about 25° C. and then filtered. The filtrate was dried under reduced pressure to give an orange-red colored product. The product was washed twice with hexane and dried under reduced pressure to give the desired product as a reddish-orange solid.

Polymerizations

A stirred 2.0 liter reactor was charged with 740 g of Isopar-E™ mixed alkanes solvent (available from Exxon Chemicals Inc.) and 118 g of 1-octene comonomer. Hydrogen was added as a molecular weight control agent by differential pressure expansion from a 75 mL addition tank at 25 psi (2070 kPa). The reactor was heated to the polymerization temperature of 140° C. and saturated with ethylene at 500 psig (3.4 MPa). Approximately 1.0 μmol of each of the above catalysts along with 1.0 mmol modified methylalumoxane (MMAO available from Akzo Chemie America Inc.) (as 0.005M solutions in toluene) were transferred to a catalyst addition tank and injected into the reactor. The polymerization conditions were maintained for 15 minutes (29 minutes for run 1) with ethylene on demand. The resulting solution was removed from the reactor, and 67 mg of a hindered phenol antioxidant (Irganox™ 1010 from Ciba Geigy Corporation) and 133 mg of a phosphorus stabilizer (Irgafos 168 from Ciba Geigy Corporation) were added. Polymers were recovered by drying in a vacuum oven set at 120° C. for about 20 hours. Results are contained in Table 1.

TABLE 1

| Run | Catalyst | Yield (g) | Efficiency Kg/gZr | Density | Melt Index[1] |
|---|---|---|---|---|---|
| 1 | Ex. 1 | 4.5 | 0.016 | — | 30 |
| 2 | Ex. 2 | 75.1 | 0.270 | .949 | 19 |
| 3 | Ex. 3 | 2.8 | 0.015 | .953 | 9.4 |
| 4 | Ex. 4 | 49.2 | 0.540 | .946 | 54 |
| 5 | Ex. 5 | 17.9 | 0.196 | .945 | 1084 |

[1]measured by micro melt index, equivalent to I2

What is claimed is:

1. A catalyst composition for addition polymerization comprising a metal complex corresponding to the formula:

$$\begin{array}{c} Z - L' \\ | \quad | \quad X'_q \\ L - M - (X)_n \end{array} \quad (I)$$

wherein:

M is a Group 4 metal in the +2, +3, or +4 formal oxidation state;

L is a group containing a divalent cyclic or noncyclic, non-aromatic, anionic, dienyl ligand group bound to M and Z, said L group containing up to 60 nonhydrogen atoms;

Z is a divalent moiety covalently bound to both L and L', comprising boron, or a member of Group 14 of the Periodic Table of the Elements, said moiety having up to 60 non-hydrogen atoms;

L' is L or an anionic, aromatic ligand group bonded to M via delocalized π-electrons, said L' group having up to 60 nonhydrogen atoms;

X' independently each occurrence is a Lewis base containing up to 40 nonhydrogen atoms;

X independently each occurrence is a monovalent anionic moiety having up to 20 non-hydrogen atoms, provided however that neither X is an aromatic group that is π-bonded to M; optionally, two X groups may be covalently bound together forming a divalent dianionic moiety having both valences bound to M; or two X groups together form a neutral, conjugated or nonconjugated diene that is π-bonded to M (whereupon M is in the +2 oxidation state); or further optionally one or more X and one or more X' groups may be bonded together thereby forming a moiety that is both covalently bound to M and coordinated thereto by means of Lewis base functionality;

n is zero, one or two; and q is a number from 0 to 3, and an activating cocatalyst.

2. A catalyst composition according to claim 1 wherein L is a divalent derivative of a pentadienyl-, cyclohexadienyl-, cyclosilahexadienyl-, cycloheptadienyl-, or cyclooctadienyl- group, a hydrocarbyl-, silyl-, dihydrocarbylamino, hydrocarbyloxy- or siloxy- substituted derivative thereof, a partially hydrogenated anthracenyl or naphthalenyl group or a hydrocarbyl-, silyl-, dihydrocarbylamino, hydrocarbyloxy- or siloxy- substituted derivative thereof; or a diphenylmethyl group.

3. A catalyst composition according to claim 1 wherein L corresponds to the formula:

wherein:

R' in each occurrence is a moiety that is independently selected from the group consisting of hydrogen, hydrocarbyl, silyl, germyl, siloxy, amino, 1o hydrocarbyloxy, cyano, halo and combinations thereof, said R' having up to 20 non-hydrogen atoms, and optionally, two or more R' groups (where R' is not hydrogen, halo or cyano) may together form a divalent derivative of one of the foregoing moieties; and provided further that one R' comprises a covalent bond to Z.

4. A catalyst composition according to claim 1 wherein the metal complex corresponds to the formula:

$$\begin{array}{c} Z - L' \\ | \quad | \\ L - M - (X)_n \end{array}$$

wherein:

Z is $SiR^*_2$, $CR^*_2$, $SiR^*_2SiR^*_2$, $CR^*_2CR^*_2$, $CR^*=CR^*$, $CR^*_2SiR^*_2$, $CR^*_2CR^*_2CR^*_2$, $CR^*_2SiR^*_2CR^*_2$, $SiR^*_2CR^*_2CR^*_2$, $SiR^*_2CR^*_2SiR^*_2$, $SiR^*_2SiR^*_2CR^*_2$, $SiR^*_2SiR^*_2SiR^*_2$, $SnR^*_2$, or $GeR^*_2$;

wherein:

R* each occurrence is independently hydrogen, or a member selected from hydrocarbyl, silyl, hydrocarbyloxy, dihydrocarbylamino, siloxy, halogenated alkyl, halogenated aryl, and combinations thereof, said R* having up to 18 non-hydrogen atoms, and optionally (when R* is not hydrogen), two R* groups from Z, or an R* group from Z and an R' group from L or L' form a ring system.

M is titanium or zirconium in the $^+2$, +3, or $^+4$ formal oxidation state;

L is a divalent derivative of a pentadienyl, cyclohexadienyl, cyclosilahexadienyl, partially hydrogenated naphthalenyl, partially hydrogenated anthracenyl group or a hydrocarbyl or silyl substituted derivative of such cyclohexadienyl, cyclosilahexadienyl, partially hydrogenated naphthalenyl, partially hydrogenated anthracenyl group, each said hydrocarbyl or silyl substituent having up to 10 nonhydrogen atoms;

L' is L or a divalent derivative of a cyclopentadienyl, fluorenyl or indenyl group, a hydrocarbyl or silyl substituted derivative thereof, or a partially hydrogenated derivative thereof, said L' having up to 50 non-hydrogen atoms;

n is one or two, and when n is two, M is in the +4 formal oxidation state and X is halo, hydrocarbyl, or hydrocarbyloxy, said X having up to 12 non-hydrogen atoms, when n is one, M is in the +2 formal oxidation state; and X is a neutral conjugated diene of from 5 to 30 carbons.

5. A catalyst composition according to claim 1, wherein the metal complex corresponds to the formula:

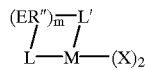

wherein:

E is independently each occurrence silicon or carbon.

R" is independently each occurrence hydrogen or $C_{1-10}$ hydrocarbyl;

L' is cyclopentadienyl, indenyl or a $C_{1-20}$ hydrocarbyl substituted or multiply substituted derivative thereof;

M is titanium in the +4 formal oxidation state;

m is an integer from 1 to 3;

L is a (2,4-disubstituted pentadien-3-yl), (2,4-disubstituted pentadien-1-yl), (1,5-disubstituted pentadien-3-yl), (6,6-disubstituted-$\eta^5$-cyclohexadien-3-yl), (6,6-disubstituted-$\eta^5$-cyclosilahexadien-3-yl), (1,2,3,4,5-pentasubstituted-$\eta$-cyclohexadien-6-yl), (1,2,3,4,5,6-hexasubstituted-$\eta$-cyclohexadien-6-yl), (1,2,4,5,6,6-hexasubstituted-$\eta^5$-cyclohexadien-3-yl)-, (1,1-disubstituted-$\eta^5$-hexahydronaphthalen-4-yl), (1,1,2,3-tetrasubstituted-$\eta^5$-hexahydronaphthalen-4-yl), or (9,9-disubstituted-10,11,12,13,14-$\eta$-1,2,3,4, 5,6,7,8,9,10-decahydroanthracene-10-yl), said substituents independently each occurrence being hydrocarbyl, hydrocarbyloxy, silyl, siloxy or a mixture thereof of up to 10 nonhydrogen atoms each; and X is methyl, phenyl, benzyl, trimethylsilylmethyl, chloro, methoxy, or ethoxy.

6. A polymerization process comprising contacting an addition polymerizable monomer with a catalyst under polymerization conditions characterized in that the catalyst comprises a catalyst composition according to claims 1 through 5.

* * * * *

UNITED STATES PATENT AND TRADEMARK OFFICE
CERTIFICATE OF CORRECTION

PATENT NO. : 6,034,021

DATED : March 7, 2000

INVENTOR(S) : David R. Wilson, et al

It is certified that error appears in the above-indentified patent and that said Letters Patent is hereby corrected as shown below:

Title Page, column 2, third reference cited, "5,098,867" should correctly read --5,096,867--.

Signed and Sealed this

Third Day of April, 2001

Attest:

NICHOLAS P. GODICI

*Attesting Officer*     Acting Director of the United States Patent and Trademark Office